(12) United States Patent
Wu et al.

(10) Patent No.: US 6,852,248 B1
(45) Date of Patent: Feb. 8, 2005

(54) DOPANTS FOR LIQUID-CRYSTAL DEVICES (75) Inventors: Shin-Tson Wu, Northridge, CA (US); Seth Marder, Tuscon, AZ (US); Qing T. Zhang, Dallas, TX (US)

(73) Assignees: HRL Laboratories, LLC, Malibu, CA (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 09/285,937

(22) Filed: Apr. 2, 1999

(51) Int. Cl.$^7$ .................. C09K 15/52; C09K 19/54; C09K 19/58
(52) U.S. Cl. ............... 252/299.01; 252/299.5; 252/299.2; 428/1.1
(58) Field of Search .................. 252/299.01, 299.5, 252/299.2, 299.6; 428/1.1

(56) References Cited

U.S. PATENT DOCUMENTS

| | | | |
|---|---|---|---|
| 2,882,158 A | 4/1959 | Brooker et al. | ............... 96/102 |
| 5,456,859 A | 10/1995 | Gray et al. | ............ 252/299.63 |
| 5,626,792 A | * 5/1997 | Wand et al. | ........... 252/299.01 |

FOREIGN PATENT DOCUMENTS

EP      0 530 784 A2     3/1993

OTHER PUBLICATIONS

CA 129: 44683, 1998.*
CA 125: 41250, 1996.*
CA 74: 12468, 1970.*
CA 111: 154088, 1989.*
CAPLUS 1992: 407540.*
Cheng, L.T., et al., "Experimental Investigations of Organic Molecular Nonlinear Optical Polarizabilities. 2. A Study of Conjugation Dependencies," *J. Phys. Chem.,* vol. 95, pp. 10643–10652 (1991).
Wu et al. "High Solubility and Low Viscosity Dyes for Guest–Host Displays," *Asia Display '95,* pp. 567–570 (1995).
Kippelen et al. "Infrared Photorefractive Polymers and Their Applications for Imaging," *Science* vol. 279, pp. 54–57 (1998).
White et al. "New absorptive mode reflective liquid–crystal display device," *Journal of Applied Physics* vol. 45 No. 11, pp. 4718–4723 (1974).
Yang, et al. "Cholesteric reflective display: Drive scheme and contrast," *Appl. Phys. Lett.* vol. 64 No. 15, pp. 1905–1907 (1994).
Piers et al. "Alkylation of 1,5–Dymethoxy–1,4–cyclohexadiene. A Convenient Synthesis of 2–Alkyl– and 2–Alkenyl–1,3–cyclohexanediones," *Journal of Organic Chemistry* vol. 42 No. 23, pp. 3755–3757 (1977).
Weinstein et al. "Reduction of 2,7–Dimethoxynaphthalene," *Journal of Organic Chemistry* vol. 30, pp. 3209–3211 (1965).
Lemke. "Knoevenagel–Kondensationen in Dimethylformamid," *Synthesis,* pp. 359–361 (1974).
Fatiadi. "New Applications of Malononitrile in Organic Chemistry–Part 1," *Synthesis,* pp. 165–204 (1978).
Wu et al. "Experimental confirmation of the Osipov–Terentjev theory on the viscosity of nematic liquid crystals," *Physical Review A* vol. 42 No. 4, pp. 2219–2227 (1990).
Wu et al. "Liquid crystal dyes with high solubility and large dielectric anisotropy," *Applied Physics Letter* vol. 64, No. 17, pp. 2191–2193 (1994).
Wu et al. "High Dielectric Dopants for Low Voltage Liquid Crystal Operation," *Japanese Journal of Applied Physics* vol. 37 Part 2 No. 10B, pp. L1254–L1256 (1998).
Wu et al. "Absorption and scattering measurements of nematic liquid crystals," *Applied Optics* vol. 26 No. 9, pp. 1722–1727 (1987).
Khoo et al. "Optics and Nonlinear Optics of Liquid Crystals," *World Scientific,* Singapore (1993).
Gudriniece, E., et al., "Condensation of dicarbonyl compounds with malononitrile," *Chemical Abstracts,* vol. 78, No. 9, abstract No. 57823k, p. 471 (Mar. 5, 1973).
Kippelen, B., et al., "Infrared Photorefractive Polymers and Their Applications for Imaging," *Science,* vol. 279, p. 54–57, (Jan. 2, 1998).
English–language abstract from *Patent Abstracts of Japan* (Aug. 16, 1985) for Kanto Kagaku KK's Japanese Patent Document No. 60069059 (Apr. 19, 1985).

* cited by examiner

*Primary Examiner*—Shean C. Wu
(74) *Attorney, Agent, or Firm*—Ladas & Parry (57) ABSTRACT

High-dielectric colorless or virtually colorless dopants for low-voltage and tunable clearing temperature liquid-crystal devices. These dopant compounds help reduce the operation voltage for both polar and non-polar liquid-crystal (LC) mixtures. Methods for making and using these dopant compounds are also disclosed.

56 Claims, 2 Drawing Sheets

DOPANTS FOR LIQUID-CRYSTAL DEVICES

STATEMENT REGARDING FEDERALLY SPONSORED RESEARCH OR DEVELOPMENT

This invention was made with United States government support under Contract No. F49620-97-1-0014 awarded by the Air Force Office of Scientific Research (AFOSR). The United States government has certain rights in this invention.

BACKGROUND

This invention concerns high-dielectric colorless or virtually colorless dopants for low-voltage and tunable clearing temperature liquid-crystal devices.

A few high dielectric anisotropy compounds have been reported in the literature.

For example, Wu et al., *Asia Display*, pp. 567–70 (1995) discloses nitro-amino azobenzenes and tolanes with the following structures:

In another example, Kippelen et al., *Science* 279, 54 (1998) discloses bicyano-amino polyene dyes with the following structure:

A general problem with the compounds and dyes disclosed by Wu et al. and Kippelen et al. is that their absorption is too large in the visible region. As a result, their light transmission is greatly reduced. This is particularly undesirable for some displays and electro-optic modulators where high transmittance is required.

SUMMARY

The invention involves new colorless or virtually colorless dopant compounds that exhibit an extraordinarily large dielectric anisotropy, a reduced elastic constant, and relatively low viscosity when mixed with liquid crystals. Therefore, adding a few percent of such dopant compounds to a liquid-crystal mixture reduces its operation voltage significantly. The low-voltage operation enables a low-cost electronic driver to be used. In addition, the clearing temperature and birefringence of the mixture can be tuned by simply adjusting the concentration of the dopants.

DESCRIPTION

The dopant compounds of the present invention are colorless or virtually colorless. That is, their absorption in the visible region is very small. (Typically, the absorption loss in the visible region or spectrum at room temperature (e.g., approximately 20–30° C. or approximately 22° C.) is greater than or equal to 0 (or about 0.01%) and less than or equal to about 5%; preferably, the absorption loss in the visible region is greater than or equal to 0 (or about 0.01%) and less than or equal to about 1%; more preferably, the absorption loss in the visible region is greater than or equal to 0 (or about 0.01%) and less than or equal to about 0.05%; even more preferably, the absorption loss in the visible region is greater than or equal to 0 and less than or equal to about 0.01%; and ideally the absorption loss in the visible region is close to 0.) Absorption loss is defined as the percentage of the input light that is absorbed by the medium.

The dopant compounds of the present invention also possess a very large dielectric anisotropy at room temperature of approximately 20–30° C. or approximately 22° C. (e.g., greater than about 50; preferably greater than about 60; and more preferably greater than about 70) and a low viscosity at room temperature of approximately 20–30° C. or approximately 22° C. (e.g., lower than about 50 centi-poise; preferably lower than about 30 centi-poise; and more preferably lower than about 15 centi-poise).

These dopant compounds help reduce the operation voltage for both polar and non-polar liquid-crystal (LC) mixtures. In addition, the nematic range and birefringence of LC mixtures can be tuned by adjusting the concentration of the dopant compounds of the present invention. That is, these dopant compounds can be used to tune the clearing temperature of LC mixtures.

Thus, the invention includes a composition comprising one or more of the dopant compounds and a liquid-crystal mixture. (A liquid-crystal mixture may comprise or consist of only one liquid-crystal compound or may comprise or consist of two or more liquid-crystal compounds, wherein a liquid-crystal compound is a compound that exhibits a liquid-crystal phase. Examples of liquid-crystal mixtures include, but are not necessarilty limited to, Merck's E7™ liquid-crystal mixture, Merck's E63™ liquid-crystal mixture, and Merck's ZLI-2359™ liquid-crystal mixture. The reason for mixing two or more LC compounds to yield an LC mixture is to widen the LC mixture's temperature range (i.e., the range from the melting point to the clearing point) because a single LC compound may not have a wide enough temperature range. The usually preferred storage temperature for an LC device is from about –40° C. to about 80° C. When two or more LC compounds are mixed in the proper concentration, the melting point of the resulting mixture may drop to the lowest available melting point.) The dopant compound or compounds may comprise any percentage of the composition. Thus, the dopant compound or compounds may comprise by weight about 99% or less of the composition; the dopant compound or compounds may comprise by weight about 75% or less of the composition; the dopant compound or compounds may comprise by weight about 50% or less of the composition; the dopant compound or compounds may comprise by weight about 25% or less of the composition; the dopant compound or compounds may comprise by weight about 15% or less of the composition; the dopant compound or compounds may comprise by weight about 10% or less of the composition; the dopant compound or compounds may comprise by weight about 5% or less of the composition; the dopant compound or compounds may comprise by weight about 3% or less of the composition; and the dopant compound or compounds may comprise by weight about 1% or less of the composition.

The composition described in the preceding paragraph preferably has at room temperature of approximately 20–30° C. (or approximately 22° C.) a relatively high $\partial n/\partial T$ (e.g., greater than about 0.005, or more preferably greater than about 0.01 or greater than about 0.05), wherein n is a refractive index of the composition at a visible wavelength (e.g., about 4000 Å to about 7000 Å or, more specifically, about 633 nm)) and T is the temperature of the composition in ° C. The $\partial n/\partial T$ represents the rate of refractive index change versus the temperature; and, thus, the unit measurement of $\partial n/\partial T$ in ° C.$^{-1}$. The larger the $\partial n/\partial T$, the lower the laser power needed for realizing the nonlinear refraction effect, which is desirable.

The invention includes a method for increasing $\partial n/\partial T$ of a liquid-crystal mixture, the method comprising adding one or more of the dopant compounds to the liquid-crystal mixture to yield a resulting mixture. The invention also includes a method for reducing an operation voltage of a liquid-crystal mixture, the method comprising adding one or more of the dopant compounds to the liquid-crystal mixture to yield a resulting mixture. The invention includes a method for tuning a clearing temperature of a liquid-crystal mixture, the method comprising adding one or more of the dopant compounds to the liquid-crystal mixture to yield a resulting mixture. In addition, the invention includes a method for tuning birefringence of a liquid-crystal mixture, the method comprising adding one or more of the dopant compounds to the liquid-crystal mixture to yield a resulting mixture. The dopant compound or compounds may comprise any percentage of the resulting mixture. Thus, the dopant compound or compounds may comprise by weight about 99% or less of the resulting mixture; the dopant compound or compounds may comprise by weight about 75% or less of the resulting mixture; the dopant compound or compounds may comprise by weight about 50% or less of the resulting mixture; the dopant compound or compounds may comprise by weight about 25% or less of the resulting mixture; the dopant compound or compounds may comprise by weight about 15% or less of the resulting mixture; the dopant compound or compounds may comprise by weight about 10% or less of the resulting mixture; the dopant compound or compounds may comprise by weight about 5% or less of the resulting mixture; the dopant compound or compounds may comprise by weight about 3% or less of the resulting mixture; and the dopant compound or compounds may comprise by weight about 1% or less of the resulting mixture.

The low voltage operation of an LC device is highly desirable because it enables a low cost electronic driver to be used. Low threshold LC mixtures are particularly attractive for the cholesteric-LC display where the threshold voltage ($V_{th}$) increases as the pitch length decreases. (D. L. White and G. N. Taylor, *J. Appl. Phys.* 45, 4718 (1974)) The recently developed polymer-stabilized cholesteric displays exhibit an excellent brightness and wide viewing angle. However, their operation voltage remain quite high (~50 $V_{rms}$, wherein $V_{rms}$ represents root-mean-square voltage). (D. K. Yang, et al., Appl. Phys. Lett. 64, 1905 (1994))

Consequently, there is an urgent need to reduce the operation voltage of these LC devices.

Based on the Freedericksz transition, the $V_{th}$ of a homogeneously aligned LC cell is governed by the splay elastic constant ($K_{11}$) and dielectric anisotropy ($\Delta\epsilon$) of the LC material according to the formula: $V_{th}=\pi(K_{11}/\Delta\epsilon)^{1/2}$. A simple way to reduce $V_{th}$ is to use high $\Delta\epsilon$ LC's, i.e., polar LC's with a large dipole moment, such as cyano group. Several cyano-biphenyl LC's (e.g., 4-cyano-4'-n-pentylbiphenyl (5CB)) do exhibit a large dielectric anisotropy ($\Delta\epsilon$ ~10) and a relatively low melting point. These compounds have become the major components of many commercial LC mixtures, despite the fact that their clearing temperature ($T_c$) is not sufficiently high. To enhance the clearing point of LC mixtures, some high-$T_c$ components are added. A general trend for the high-$T_c$ LC compounds is that their melting point is also very high. For example, the melting-point temperatures ($T_{mp}$) of cyano-terphenyl (5CT) and cyano-diphenyl-diacetylene (PTTP-6CN) are 131° C. and 145.3° C., respectively. A high melting point implies that the compound will have a poor solubility for forming eutectic mixtures.

In this disclosure, we present some colorless (or virtually colorless), high-dielectric compounds for use as dopant materials for lowering the $V_{th}$ of LC mixtures. Since these dopants possess a huge dielectric anisotropy, adding ~3% of such a dopant to an LC mixture is enough to significantly reduce $V_{th}$ while keeping viscosity low.

The invention comprises compounds illustrated below by the following formula A:

wherein X is selected from the group consisting of and ;

wherein D is selected from the group consisting of $NR_aR_b$, $OR_a$, $SR_a$, $PR_aR_b$, and $R_c$;
wherein A is selected from the group consisting of:

wherein $R_a$, $R_b$, and $R_c$ are the same or different and are each independently selected from the group consisting of: H; a linear, branched, or cyclic alkyl group; —$(CH_2CH_2O)_\alpha$—$(CH_2)_\beta OR_{A1}$; —$(CH_2CH_2O)_\alpha$—$(CH_2)_\beta NR_{A2}R_{A3}$; —$(CH_2CH_2O)_\alpha$—$(CH_2)_\beta CN$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$; —$(CH_2CH_2O)_\alpha$—$(CH_2)_\beta$-Phenyl; —$(CH_2)_\alpha(CF_2)_\gamma CF_3$; and an aryl group;
wherein $R_d$, $R_e$, $R_f$, $R_l$, $R_m$, $R_n$, $R_o$, $R_p$, $R_q$, $R_r$, $R_s$, $R_t$, $R_u$, $R_v$, $R_w$, and $R_x$ are the same or different and are each independently selected from the group consisting of: H; a linear, branched, or cyclic hydrocarbon group that is saturated or unsaturated; a linear, branched, or cyclic alkyl group; $-(CH_2CH_2O)_\alpha-(CH_2)_\beta OR_{A1}$; $-(CH_2CH_2O)_\alpha-(CH_2)_\beta NR_{A2}R_{A3}$; $-(CH_2CH_2O)_\alpha-(CH_2)_\beta CN$; $-(CH_2CH_2O)_\alpha-(CH_2)_\beta Cl$; $-(CH_2CH_2O)_\alpha-(CH_2)_\beta Br$; $-(CH_2CH_2O)_\alpha-(CH_2)_\beta I$; $-(CH_2CH_2O)_\alpha-(CH_2)_\beta$-Phenyl; $-(CH_2)_\alpha(CF_2)_\gamma CF_3$; and an aryl group;

wherein $R_g$, $R_h$, $R_i$, and $R_k$ are the same or different and are each independently selected from the group consisting of: H; a linear, branched, or cyclic hydrocarbon group that is saturated or unsaturated; a linear, branched, or cyclic alkyl group; $-(CH_2CH_2O)_\alpha-(CH_2)_\beta OR_{A1}$; $-(CH_2CH_2O)_\alpha-(CH_2)_\beta NR_{A2}R_{A3}$; $-(CH_2CH_2O)_\alpha-(CH_2)_\beta CN$; $-(CH_2CH_2O)_\alpha-(CH_2)_\beta Cl$; $-(CH_2CH_2O)_\alpha-(CH_2)_\beta Br$; $-(CH_2CH_2O)_\alpha-(CH_2)_\beta I$; $-(CH_2CH_2O)_\alpha-(CH_2)_\beta$-Phenyl; an aryl group; $-(CH_2)_\alpha(CF_2)_\gamma CF_3$; $-CO_2R_d$; and $-COR_d$;

wherein each aryl group is optionally independently selected from the group consisting of wherein $R_{A1}$, $R_{A2}$, $R_{A3}$, $R_{A4}$, $R_{A5}$, $R_{A6}$, $R_{A7}$, and $R_{A8}$ are the same or different and are each independently selected from the group consisting of H, a linear alkyl group, a branched alkyl group, and a cyclic alkyl group;

wherein E is selected from the group consisting of S, O, and $NR_s$;

wherein the linear, branched, or cyclic hydrocarbon group that is saturated or unsaturated optionally includes up to 25 (or 8 or 5) carbon atoms (exemplary unsaturated hydrocarbons include, but are not necessarily limited to, ethylene, propylene, butene, methylpropene, pentene, hexene, methylbutene, ethyne, propyne, butyne, pentyne, hexyne, cyclopropene, cyclobutene, cyclopentene, cyclohexene, cycloheptene, cyclooctene, cyclononene, cyclobutadiene, and cyclohexadiene; examplary saturated hydrocarbons are set forth in the next paragraph);

wherein the linear, branched, or cyclic alkyl group optionally includes up to 25 (or 8 or 5) carbon atoms (exemplary alkyl groups include, but are not necessarily limited to, methyl, ethyl, propyl, butyl, pentyl, hexyl, heptyl, octyl, and nonyl, in the normal, secondary, iso, and neo attachment isomers; cyclopropane; cyclbutane; cyclopentane; cyclohexane; cycloheptane; cyclooctane; cyclononane; and decalin);

wherein α is an integer that is greater than or equal to 0 and less than or equal to 25 (or less than or equal to 8 or 5 or 2 or 1);

wherein β is an integer that is greater than or equal to 0 and less than or equal to 25 (or less than or equal to 8 or 5 or 2 or 1);

wherein γ is an integer that is greater than or equal to 0 and less than or equal to 25 (or less than or equal to 8 or 5 or 2 or 1);

wherein when D is $NR_aR_b$, then α optionally is greater than or equal to 1 and less than or equal to 25;

wherein when $R_l$, $R_m$, $R_n$, $R_q$, and $R_r$ are each H, and $R_o$, $R_p$, and D are each $-CH_3$, A optionally is not C(CN)(CN);

wherein when $R_l$, $R_m$, $R_n$, $R_o$, and $R_p$ are each H and $R_q$, $R_r$, and D are each $-CH_3$, A optionally is not C(CN)(CN);

wherein when $R_l$, $R_o$, $R_p$, $R_q$, and $R_r$ are each H, and $R_n$, $R_m$, and D are each $-CH_3$, A optionally is not C(CN)(CN);

wherein when $R_l$, $R_m$, $R_n$, $R_o$, $R_p$, $R_q$, and $R_r$ are each H, and D is $-CH_3$, A optionally is not C(CN)(CN); and wherein * represents an attachment point (e.g., the attachment point at which A attaches to X).

In one embodiment, preferably in formula A, $R_l$, $R_m$, $R_n$, $R_o$, $R_p$, $R_q$, $R_r$, $R_t$, $R_u$, $R_v$, $R_w$, and $R_x$ are each H, A is C(CN)(CN), and D is $R_y$ or $OR_y$, wherein $R_y$ is selected from the group consisting of a linear alkyl group, a branched alkyl group, and an aryl group.

The procedures for making the above-described compounds are set forth below schematically.

Procedure 1:

The first step in procedure 1 (i.e., the step that uses compound I to make compound II) is called a Birch reduction. The Birch reduction is described in greater detail in the following two articles, which are incorporated herein by this reference: E. Piers, J. R. Grierson, *J. Org. Chem.*, 1977, 42, 3755–3757; and P. Radlick, *J. Org. Chem.*, 1965, 30, 3209–3211. The last step in procedure 1 (i.e., the step that uses compound IV to make compound V) and below-described procedures 3a, 3b, 3c, and 3d are called Knoevenagel condensation reactions. Knoevenagel condensation reactions are described in greater detail in the following two articles, which are incorporated herein by this reference: R. Lemke, *Synthesis*, 1974, 359–361; and A. J. Fatiadi, *Synthesis*, 1978, 165–204.

Procedure 2a:

Procedure 2b:

In procedure 2d, $R_a$ and $R_b$ are not both aryl groups.

Procedure 2c:

In procedure 2c, $R_a$ and $R_b$ are not both aryl groups.

Procedure 3a:

Procedure 3b:

Procedure 3c:

Procedure 3d:

In the procedure described above, $AH_2$ is selected from the group consisting of:

Compounds wherein D is $SR_a$ may be made by a procedure analogous to procedure 2a above; and compounds wherein D is $PR_aR_b$ may be made by a procedure analogous to procedure 2b above.

Four compounds of the above-described invention were studied. Their molecular structures are shown below in formulas I–IV.

(I)

-continued (II)

(III)

(IV)

The melting point (in °C.) and heat fusion enthalpy (in kcal/mol) of compounds I–IV are set forth below in Table 1.

TABLE 1

| Compound | Melting Point (in °C.) | Heat Fusion Enthalpy (in kcal/mol) |
|---|---|---|
| Formula I | 84.0 | 5.93 |
| Formula II | 3.4 | 5.32 |
| Formula III | 74.9 | 6.35 |
| Formula IV | 61.2 | 4.98 |

There are several reasons for designing these linear polyene in molecules. First, these linear polyene molecules exhibit a considerable charge transfer that is confined along the quasi-one-dimensional π-conjugated bridge (i.e., along the bridge comprising two or more unsaturated (e.g., double) bonds). Second, the incorporation of the polyene into a ring-containing bridge prevents isomerization resulting in improved thermal and photochemical stability. Third, the ability to change alkyl groups allows one to control the melting temperature so as to tune the solubility to the LC's. Fourth, the two cyano or cyano/amino groups provide (or more broadly the A group in formula A provides) a huge push-pull effect for enhancing the dipole moment; and fifth, the cyano acceptors themselves have (or more broadly the A group in formula A has) a large group dipole moment.

The threshold voltage, visco-elastic coefficient, and absorption spectra of the compounds of formulas I–III were measured. (The compound of formula IV is a chiral material, so its physical properties were not studied.) In the sample preparation, we mixed 3% of each compound in a commercial E63™ LC mixture. (E63™ LC mixture is a Merck mixture. Its major components are alkyl cyano-biphenyl and alkoxy cyano-biphenyl. This mixture was used because it has very wide nematic range: its melting point is below −40° C. and its clearing point is about 87° C.) These guest-host mixtures were then injected into a homogeneous-aligned cell. The cell gap (i.e., the gap between substrates in a liquid-crystal display) was controlled by spacers to be about 5.6 $\mu$m, and the pretilt angle was ~2°. (The pretilt angle is the angle inclined on the liquid crystal substrates. This way, liquid crystals know which way to relax back without creating instability. A typical pretilt angle of an LC cell is 1–5°.) The voltage-dependent phase change method was used for determining the threshold voltage. (The voltage-dependent phase change method has been described in Wu, et al., *Phys. Rev. A*. 42, 2219–2227 (1990), which is incorporated herein by this reference.) Results measured at λ=633 nm are plotted in FIG. 1.

Figure 1:
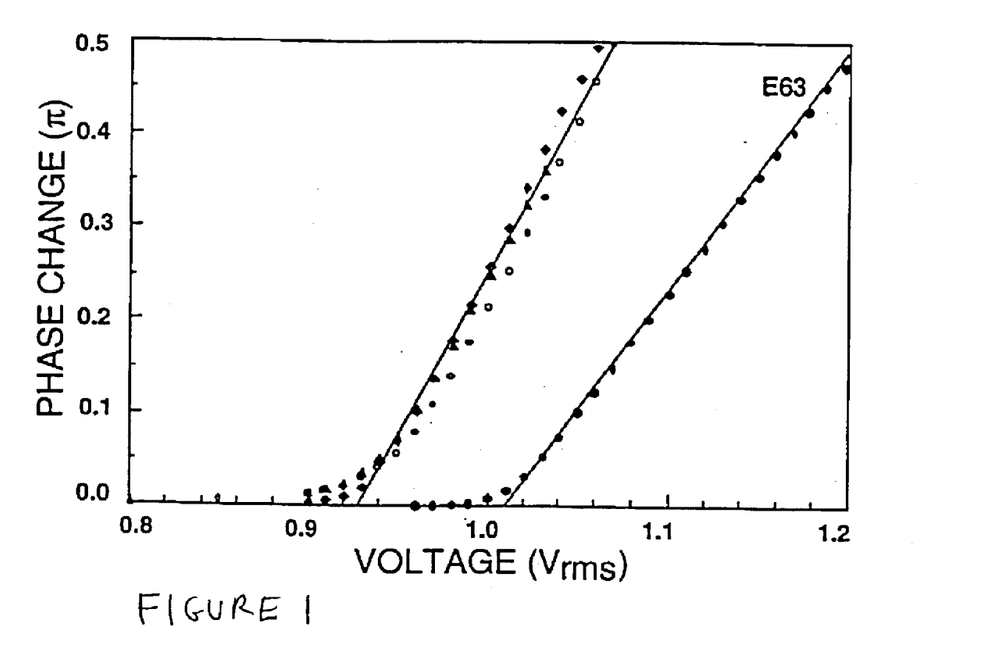
FIG. 1 is a graph showing the voltage-dependent phase change of four E63™ LC cells that were studied.

In FIG. 1, the axis labelled "Phase Change (π)" is the phase of a liquid crystal cell, wherein the phase is described as $\delta=2\pi d\Delta n/\lambda$; where d is the cell gap, $\Delta n$ is the effective birefringence and $\lambda$ is the wavelength. When a voltage is applied to the liquid crystal cell, the effective birefringence is decreased as the applied voltage is increased. Thus, a phase change 0.5π means $\delta(V=0)-\delta(V)=2\pi d[\Delta n(V=0)-\Delta n(V)]/\lambda=0.5\pi$.

In FIG. 1, the solid circles represent experimental data of pure E63™ LC mixture; the open circles are for 3% of the compound of formula I dissolved in E63™ LC mixture (i.e., 3% by weight of the total mixture of the compound of formula I and the E63™ LC mixture); the diamonds are for 3% of the compound of formula II dissolved in E63™ LC mixture (i.e., 3% by weight of the total mixture of the compound of formula II and the E63™ LC mixture); and the triangles are for 3% of the compound of formula III dissolved in E63™ LC mixture (i.e., 3% by weight of the total mixture of the compound of formula III and the E63™ LC mixture).

Results for the compounds of formulas I, II, and III overlap closely due to their similar structures. In the vicinity of threshold voltage, the voltage-dependent phase change is linear. From this linear extrapolation, the threshold voltage is obtained. From FIG. 1, the $V_{th}$ of E63™ LC mixture at f=2 KHz (f=2 KHz means the frequency of the applied AC voltage) and room temperature (approximately 22° C.) is found to be ~1.01 $V_{rms}$. Adding 3% by weight of the compounds of formulas I, II and III lowers the threshold voltage to 0.93 $V_{rms}$. Knowing that E63™ LC mixture's $\Delta\epsilon$ is 14.6, we estimate that the $\Delta\epsilon$ of the compounds of formulas I, II, and III is extrapolated to be about 50. The observed dielectric anisotropy in the compounds of the present invention is similar to the dielectric anisotropy of the nitro-amino azobenzenes and tolans described in S. T. Wu, et al., *Appl. Phys. Lett.* 64, 2191 (1994) and *Asia Display* pp. 567 (1995), and is smaller than the dielectric anisotropy of the bicyano-amino polyenes described in Wu, et al., *Jpn. J. Appl. Phys.* 37, L1254–56 (1998). However, these previously reported compounds are colored. They have strong absorption in the visible region; and, thus, use of these previously reported compounds is limited.

Increasing dopant concentration would further reduce threshold voltage at the price of increased mixture viscosity. To evaluate the viscosity of these compounds, the decay time was measured for these LC cells with 3% concentrations (by weight) of the compounds of formulas I, II, and III. Through time-dependent phase change measurements, the visco-elastic coefficients ($\gamma_1/K_{11}$) of the guest-host mixtures were determined. (The time-dependent phase change method has been described in Wu, et al., *Phys. Rev. A*. 42, 2219–2227 (1990).) The measured visco-elastic coefficient ($\gamma_1/K_{11}$) for 3% of the compound of formula I dissolved in E63™ LC mixture was 20 ms/$\mu$m²; the measured visco-elastic coefficient ($\gamma_1/K_{11}$) for 3% of the compound of formula II dissolved in E63™ LC mixture was 23.8 ms/$\mu$m²; and the measured visco-elastic coefficient ($\gamma_1/K_{11}$) for 3% of the compound of formula III dissolved in E63™ LC mixture was 23.7 ms/$\mu$m².

The viscosity of an LC compound is determined by its moment of if inertia, molecular shape, and temperature. The compound of formula I has the lowest viscosity as expected from theory because it has the shortest or smallest side chain (i.e., the shortest or smallest D group). (Wu, et al., *Jpn. J. Appl. Phys.* 37, L1254–56 (1998).) According to this theory, the smaller X group is in formula A, the lower the viscosity and the higher the melting point and the clearing temperature.

Figure 2:
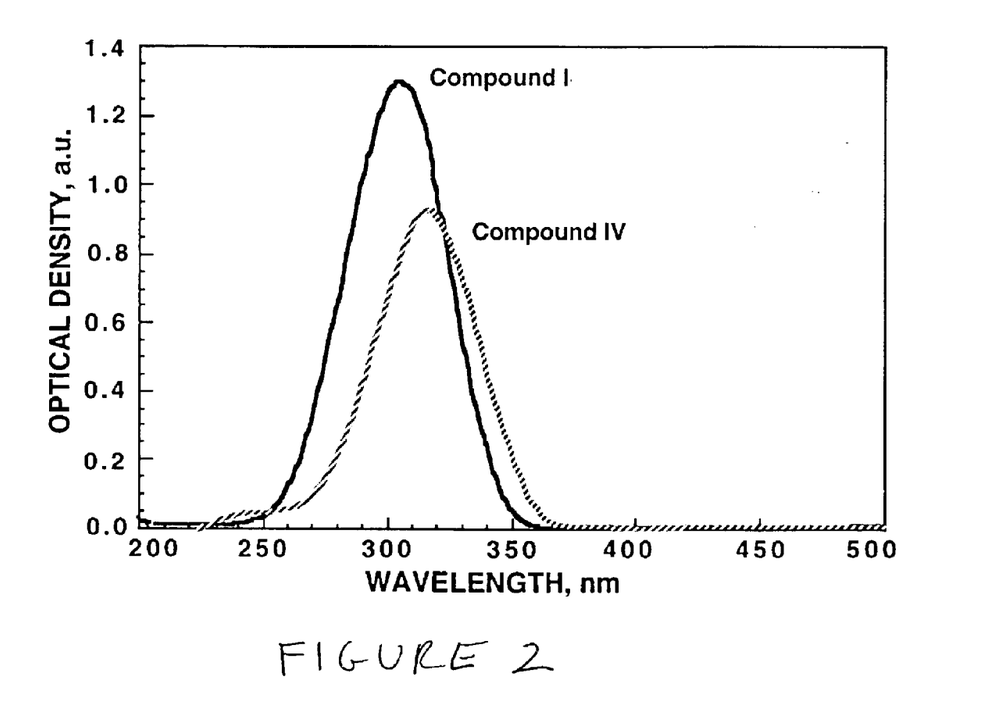
FIG. 2 is a graph showing the optical density of 1% the compound of formula I in a ZLI-2359™ LC mixture and the optical density of 1% the compound of formula IV in an ZLI-2359™ LC mixture.

The absorption spectra of the compounds of formulas I, II, and III are nearly identical because of the structural similarity of these compounds. To measure absorption, 1% of the compound of formula I (by weight) was dissolved in a UV transparent LC host, ZLI-2359™ LC mixture; and 1% of the compound of formula IV (by weight) was dissolved in another ZLI-2359™ LC mixture. (ZLI-2359™ LC mixture, which is a UV transparent liquid crystal mixture made by Merck, includes some cyclohexane compounds that don't absorb UV light. Thus, ZLI-2359™ LC mixture is a good host for UV absorption measurements.) A homogeneous cell with an approximately 6-µm cell gap was used for measurements. The results are shown in FIG. 2, wherein "a.u." represents arbitrary units. FIG. 2 shows that the compounds of formula I and IV are highly transparent throughout the entire visible spectral region.

The clearing temperature ($T_c$) of such a guest-host system is reduced much faster than the linear extrapolation from a eutectic mixture: $(T_c)_{gh}=x(T_c)_g+(1-x)(T_c)_h$, wherein x is the concentration of the dopant/guest, "g" refers to the guest, and "h" refers to the host. The host mixture E63™ LC mixture's clearing-point temperature is ~87° C. When 3% of the compound of formula II is added to the host, the extrapolated clearing-point temperature ($T_c$) should be ~84.5° C., according to the formula set forth in the first sentence of this paragraph. However, the measured $T_c$ was ~65° C. This indicates that the compound of formula II causes a larger-than-expected molecular separation. This is evidenced by the fact that the mixture birefringence drops from 0.22 for pure E63™ LC mixture to 0.21 and $K_{11}$ drops from 12.6 to 11.2 pico-Newton after 3% of the compound of formula II is added to the E63™ LC mixture.

A high clearing point (e.g., about 70–100° C.) is normally preferred, but in some circumstances, a low clearing point finds interesting applications as well. For example, for nonlinear optical effects using isotropic LC's, it is important to have an LC mixture with an isotropic phase (i.e., a phase with no visible crystals) below room temperature. (The isotropic phase is the phase at which the liquid-crystalline behaviors disappear. As the temperature goes beyond the clearing temperature, the liquid crystal becomes an isotropic liquid. That means many or all the anisotropic behaviors, such as optical and dielectric anisotropy, disappear.) The light scattering of an LC at the isotropic state is 2–3 orders of magnitude lower than that in the nematic state. (S. T. Wu and K. C. Lim, *Appl. Opt.* 26, 1722–1727 (1987).) (The nematic state means the temperature range in which the nematic phase exits.

Liquid crystal exists in only a certain temperature range. The sequence of phase transition is: crystalline phase, nematic phase, and isotropic phase.)

Another potential application of this tunable $T_c$ is to control the mixture with large temperature-dependent refractive indices, $\partial n/\partial T$. It is well-known that $\partial n/\partial T$ is much enhanced when the temperature is about 2–3 degrees Cen tigrade below $T_c$. (I. C. Khoo and S. T. Wu, *Optics and Nonlinear Optics of Liquid Crystals* (World Scientific, Singapore, 1993)) For example, to operate a liquid crystal device at room temperature (e.g., 22° C.), then one must design a liquid-crystal mixture with a clearing point about 2–5 degrees Centigrade above room temperature in order to take advantage of a large $\partial n/\partial T$.

Figure 3:
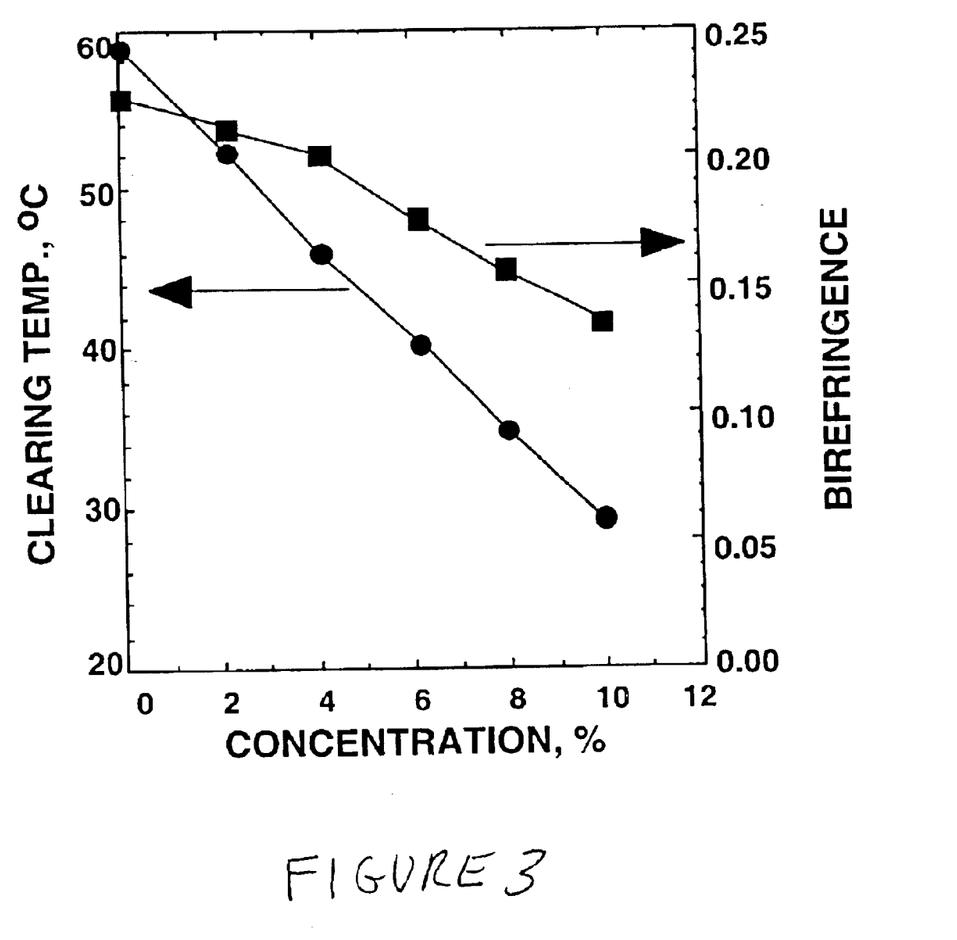
FIG. 3 is a graph showing dopant concentration-dependent clearing temperature (dots) and birefringence (squares) of an E7™ liquid-crystal mixture.

FIG. 3 shows the concentration-dependent clearing temperature (left) and birefringence (right) of a Merck E7™ liquid-crystal mixture. The compound of formula II was used as the guest dopant; and an E7™ LC mixture was used as the host. The major component of an E7™ LC mixture is cyano-biphenyl. The melting point of the E7™ LC mixture is about 59.5° C.; and Δn is about 0.224 at room temperature (about 22° C.) and λ=633 nm. As the guest concentration increased, both the clearing point and birefringence decreased almost linearly. At about 10% concentration by weight (i.e., when the guest comprised about 10% by weight of the guest-host mixture), the guest-host mixture's clearing point dropped to about 28° C.; and birefringence dropped to about 0.135. The decreased birefringence is partly related to the decreased clearing point. At a low clearing point, the corresponding order parameter of the mixture at room temperature is reduced. On the other hand, at 10% concentration, the guest-host mixture's melting temperature was suppressed to about −30° C. Thus, the 10% guest-host mixture not only had a large $\partial n/\partial T$ (the rate of refractive index change) at room temperature (about 22° C.), but also had a low melting temperature for practical applications.

The compounds of formulas I, II, III, and IV were made by a Knoevenagel reaction between ketones and malononitrile with a few drops of piperidine. Details regarding procedures 1, 2a, 2b, 2c, 3a, 3b, 3c, and 3d, which are described above, can be found in the following preparation procedures.

Preliminary Step: Preparing 3-Hexyl-2-cyclohexenone

To a solution of 3-ethoxy-2-cyclohexenone (8.62 g, 61.50 mmol) in dry THF (tetrahydrofuran), hexylmagnesuim bromide (15.38 mL, 2.0 M, 30.75 mmol) was added dropwise with stirring. The mixture was kept at 0° C. (in an ice-water bath) during the whole process and then was allowed to warm (the ice-water bath was removed) to ambient temperature (approximately 22° C.). Hydrochloric acid (10 mL, 3.0 M) was added to the above mixture. The mixture was extracted with diethylether 3 times. The combined organic layerswere washed with water and then dried over magnesium sulfate. The product was further purified by flash chromatography on silica gel using 10:100 (dicholomethane:hexane (volume:volume)) to yield 6.17 g (xx %) of 3-hexyl-2-cyclohexenone. $^1$H NMR (300 MHz, CDCl$_3$): δ 5.78 (s, 1 H), 2.40–2.20 (m,4 H), 2.20–2.10 (t, J=7.37 Hz, 2H), 1.90 (p, J=6.50 Hz, 2 H), 1.42 (t, J=7.30 Hz, 2 H), 1.22 (br, 6 H), 0.81 (t, J=6.70 Hz, 3 H). $^{13}$C NMR (75 MHz, CDCl$_3$): 200.06, 167.00, 126.04, 38.49, 37.80, 32.02, 30.11, 29.35, 27.35, 23.21, 22.95, 14.42, GC/MS calculated for C$_{12}$H$_{20}$O 180.15, found 180.15. The foregoing gas chromatography/mass spectrometry measurements confirmed the structure.

Preparing the Compound of Formula II

3-Hexyl-2-cyclohexenone (6.17 g, 34.22 mmol) and malononitrile (6.78 g, 102.63 mmol) and piperidine (2 drops (i.e. approximately 0.2 ml)) were stirred overnight (approximately 12 hours). The mixture was purified by flash chromatography on silica gel using 10:100 (dicholomethane:hexane (volume:volume)) to yield the compound of formula II (6.62 g (85%)). $^1$H NMR (300 MHz, CDCl$_3$): δ 6.57 (s, 1 H), 2.71 (t, J=6.31 Hz, 2 H), 2.31 (m, 4 H), 1.86 (p, J=6.12 Hz, 2 H), 1.51 (t, J=7.31 Hz, 2 H), 1.29 (br, 6 H), 0.88 (t, J=6.60 Hz, 3 H). $^{13}$C NMR (75 MHz, CDCl$_3$): 171.32, 167.03, 121.27, 121.08, 113.71, 112.97, 39.60, 32.03, 30.43, 29.87, 29.49, 27.83, 23.00, 22.11, 14.51. HRMS (high resolution mass spectrometry) calculated for $C_{15}H_{20}N_2$ 228.1626, found 228.1617. Elemental analysis calculated for $C_{15}H_{20}N_2$; C, 78.90; H, 8.82; N, 12.26. Found: C, 78.94; H, 8.87; N, 12.20. UV-Vis in CH$_2$Cl$_2$ λ$_{max}$=305 nm. The foregoing data confirm the final product.

Preparing the Compound of Formula I

3-Methyl-2-cyclohexen-1-one (2.0 g, 18.16 mmol), malononitrile (3.60 g, 54.47 mmol) and piperidine (3 drops (i.e., approximately 0.2 or 0.3 ml) were heated to 80° C. overnight (approximately 12 hours). The product was purified by flash chromatography with hexane:acetone (10:1 (volume:volume)) on silica gel to give 1.78 g (62%) of the compound of formula I. $^1$H NMR (300 MHz, CDCl$_3$): δ 6.63 (s, 1 H), 2.71 (t, J=6.50 Hz, 2 H), 2.35 (t, J=5.78 Hz, 2 H), 2.08 (s, 3 H), 1.90 (p, J=6.34 Hz, 2 H). $^{13}$C NMR (75 MHz, CDCl$_3$): 171.20, 162.47, 122.18, 121.08, 113.68, 112.92, 31.85, 29.57, 25.84, 21.96. Anal. calculated for $C_{10}H_{10}N_2$; C, 75.92; H, 6.37; N, 17.70. Found: C, 75.80; H, 6.42; N, 17.85. UV-Vis in CH$_2$Cl$_2$ λ$_{max}$=305 nm. The foregoing date for NMR, elemental analysis, and the compound's UV-Vis spectrometry confirm the structural identity of the final product.

Preparing the Compound of Formula IV (1s)-(-)-Verbenone (7.89 g, 52.50 mmol), malononitrile (10.05 g, 157.50 mmol), and piperidine (0.29 mL) were heated to 80° C. overnight (approximately 12 hours). The product was purified by flash chromatography with hexane:acetone (10:1) on silica gel to give 7.49 g (72%) of the compound of formula IV. $^1$H NMR (300 MHz, CDCl$_3$): δ 6.48 (s, 1 H), 3.33 (t, J=5.55 Hz, 1 H), 2.83 (q, J=5.40 Hz, 1 H), 2.49 (t, J=5.53 Hz, 1 H), 2.10 (s, 3 H), 1.92 (d, J=9.29 Hz, 1 H), 1.57 (s, 3 H), 0.93 (s, 3 H). HRMS cald for $C_{13}H_{15}N_2$ 199.1235, found 199.1232. Anal. calculated for $C_{13}H_{15}N_2$; C, 78.75; H, 7.11; N, 14.12. Found: C, 78.79; H, 7.09; N, 14.15. UV-Vis in CH$_2$Cl$_2$ λ$_{max}$=320 nm. The foregoing date for NMR, elemental analysis, and the compound's UV-Vis spectrometry confirm the structural identity of the final product.

Preparing the Compound of Formula III

The compound of formula III was synthesized in the same manner as described above for the compound of formula I. Isophorone (7.25 g, 52.46 mmol), malononitrile (10.05 g, 157.50 mmol), piperidine (0.29 mL) were heated to 80° C. overnight (approximately 12 hours). The product was purified by flash chromatography with hexane:acetone (10:1) on silica gel to give 6.89 g (73%) of the compound of formula III. $^1$H NMR (300 MHz, CDCl$_3$): δ 6.63 (s, 1 H), 2.53 (s, 2 H), 2.20 (s, 2 H), 2.05 (s, 3 H), 1.03 (s, 6 H). $^{13}$C NMR (75 MHz, CDCl$_3$): 170.88, 160.37, 121.07, 113.70, 112.92, 46.21, 43.18, 32.88, 28.33, 25.79. HRMS calculated for $C_{12}H_{14}N_2$ 185.1157, found 186.1150. Anal. calculated for $C_{12}H_{14}N_2$: C, 77.38; H, 7.57; N, 15.03. Found: C, 77.35; H, 7.59; N, 15.04. UV-Vis in CH$_2$Cl$_2$ λ$_{max}$=304 nm. The foregoing date for NMR, elemental analysis, and the compound's UV-Vis spectrometry confirm the structural identity of the final product.

All of the measurements set forth in this application are approximations.

The invention illustratively disclosed herein suitably may be practiced in the absence of any element which is not specifically disclosed herein.

The following claims are entitled to the broadest possible scope consistent with this application. The claims shall not necessarily be limited to the preferred embodiments or to the embodiments shown in the examples.

What is claimed is:

1. A composition comprising a liquid-crystal mixture and a compound having a formula A:

(formula A)

wherein X is selected from the group consisting of and
;

wherein D is selected from the group consisting of $NR_aR_b$, $OR_a$, $SR_a$, $PR_aR_b$, and $R_c$;

wherein A is selected from the group consisting of:

, and
;

wherein $R_a$, $R_b$, and $R_c$ are the same or different and are each independently selected from the group consisting of: H; a linear alkyl group; a branched alkyl group; a cyclic alkyl group; —$(CH_2CH_2O)_\alpha$—$(CH_2)_\beta OR_{A1}$; —$(CH_2CH_2O)_\alpha$—$(CH_2)_\beta NR_{A2}R_{A3}$; —$(CH_2CH_2O)_\alpha$—$(CH_2)_\beta CN$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$; —$(CH_2CH_2O)_\alpha$—$(CH_2)_\beta$-Phenyl; —$(CH_2)_\alpha(CF_2)_\gamma CF_3$; and an aryl group;

wherein $R_d$, $R_e$, $R_f$, $R_l$, $R_m$, $R_n$, $R_o$, $R_p$, $R_q$, $R_r$, $R_s$, $R_t$, $R_u$, $R_v$, $R_w$, and $R_x$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; —$(CH_2CH_2O)_\alpha$—$(CH_2)_\beta OR_{A1}$; —$(CH_2CH_2O)_\alpha$—$(CH_2)_\beta NR_{A2}R_{A3}$; —$(CH_2CH_2O)_\alpha$—$(CH_2)_\beta CN$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$; —$(CH_2CH_2O)_\alpha$—$(CH_2)_\beta$-Phenyl; —$(CH_2)_\alpha(CF_2)_\gamma CF_3$; and an aryl group; wherein the hydrocarbon group is saturated or unsaturated;

wherein $R_g$, $R_h$, $R_i$, and $R_k$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; —$(CH_2CH_2O)_\alpha$—$(CH_2)_\beta OR_{A1}$; —$(CH_2CH_2O)_\alpha$—$(CH_2)_\beta NR_{A2}R_{A3}$; —$(CH_2CH_2O)_\alpha$—$(CH_2)_\beta CN$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$; —$(CH_2CH_2O)_\alpha$—$(CH_2)_\beta$-Phenyl; an aryl group; —$(CH_2)_\alpha(CF_2)_\gamma CF_3$; —$CO_2R_d$; and —$COR_d$; wherein the hydrocarbon group is saturated or unsaturated;

wherein each aryl group is optionally independently selected from the group consisting of and
;

wherein $R_{A1}$, $R_{A2}$, $R_{A3}$, $R_{A4}$, $R_{A5}$, $R_{A6}$, $R_{A7}$, and $R_{A8}$ are the same or different and are each independently selected from the group consisting of H, a linear alkyl group, a branched alkyl group, and a cyclic alkyl group;

wherein E is selected from the group consisting of S, O, and $NR_s$;

wherein the alkyl group is optionally substituted or unsubstituted and optionally includes up to 25 carbon atoms;

wherein $\alpha$ is an integer that is greater than or equal to 0 and less than or equal to 25;

wherein $\beta$ is an integer that is greater than or equal to 0 and less than or equal to 25; and wherein $\gamma$ is an integer that is greater than or equal to 0 and less than or equal to 25.

2. A composition as claimed in claim 1, wherein the compound comprises less than or equal to about 50% by weight of the composition.

3. A method for reducing an operation voltage of a liquid-crystal mixture, the method comprising adding to the liquid-crystal mixture a compound having a formula A:

(formula A)

wherein X is selected from the group consisting of and
;

wherein D is selected from the group consisting of $NR_aR_b$, $OR_a$, $SR_a$, $PR_aR_b$, and $R_c$;

wherein A is selected from the group consisting of:

, and
;

wherein $R_a$, $R_b$, and $R_c$ are the same or different and are each independently selected from the group consisting of: H; a linear alkyl group; a branched alkl group; a cyclic alkyl group; —$(CH_2CH_2O)_\alpha$—$(CH_2)_\beta OR_{A1}$; —$(CH_2CH_2O)_\alpha$—$(CH_2)_\beta NR_{A2}R_{A3}$; —$(CH_2CH_2O)_\alpha$—$(CH_2)_\beta CN$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$; —$(CH_2CH_2O)_\alpha$—$(CH_2)_\beta$-Phenyl; —$(CH_2)_\alpha(CF_2)_\gamma CF_3$; and an aryl group;

wherein $R_d$, $R_e$, $R_f$, $R_l$, $R_m$, $R_n$, $R_o$, $R_p$, $R_q$, $R_r$, $R_s$, $R_t$, $R_u$, $R_v$, $R_w$, and $R_x$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; —(CH$_2$CH$_2$O)$_\alpha$—(CH$_2$)$_\beta$OR$_{A1}$; —(CH$_2$CH$_2$O)$_\alpha$—(CH$_2$)$_\beta$NR$_{A2}$R$_{A3}$; —(CH$_2$CH$_2$O)$_\alpha$—(CH$_2$)$_\beta$CN; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; —(CH$_2$)$_\alpha$(CF$_2$)$_\gamma$CF$_3$; and an aryl group; wherein the hydrocarbon group is saturated or unsaturated;

wherein $R_g$, $R_h$, $R_i$, and $R_k$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; —(CH$_2$CH$_2$O)$_\alpha$—(CH$_2$)$_\beta$OR$_{A1}$; —(CH$_2$CH$_2$O)$_\alpha$—(CH$_2$)$_\beta$NR$_{A2}$R$_{A3}$; —(CH$_2$CH$_2$O)$_\alpha$—(CH$_2$)$_\beta$CN; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; an aryl group; —(CH$_2$)$_\alpha$(CF$_2$)$_\gamma$CF$_3$; —CO$_2$R$_d$; and —COR$_d$; wherein the hydrocarbon group is saturated or unsaturated;

wherein each aryl group is optionally independently selected from the group consisting of wherein $R_{A1}$, $R_{A2}$, $R_{A3}$, $R_{A4}$, $R_{A5}$, $R_{A6}$, $R_{A7}$, and $R_{A8}$ are the same or different and are each independently selected from the group consisting of H, a linear alkyl group, a branched alkyl group, and a cyclic alkyl group;

wherein E is selected from the group consisting of S, O, and NR$_s$;

wherein the alkyl group is optionally substituted or unsubstituted and optionally includes up to 25 carbon atoms;

wherein $\alpha$ is an integer that is greater than or equal to 0 and less than or equal to 25;

wherein $\beta$ is an integer that is greater than or equal to 0 and less than or equal to 25; and wherein $\gamma$ is an integer that is greater than or equal to 0 and less than or equal to 25.

4. A method as claimed in claim 3, wherein an amount of the compound is added to and mixed with the liquid-crystal mixture to yield a resulting mixture, wherein the amount of the compound is less than or equal to about 50% by weight of the resulting mixture.

5. A method for tuning a clearing temperature of a liquid-crystal mixture, the method comprising adding to the liquid-crystal mixture 1 a compound having a formula A:

(formula A)

wherein X is selected from the group consisting of wherein D is selected from the group consisting of NR$_a$R$_b$, OR$_a$, SR$_a$, PR$_a$R$_b$, and R$_c$;

wherein A is selected from the group consisting of:

wherein $R_a$, $R_b$, and $R_c$ are the same or different and are each independently selected from the group consisting of: H; a linear alkyl group; a branched alkyl group; a cyclic alkyl group; —(CH$_2$CH$_2$O)$_\alpha$—(CH$_2$)$_\beta$OR$_{A1}$; —(CH$_2$CH$_2$O)$_\alpha$—(CH$_2$)$_\beta$NR$_{A2}$R$_{A3}$; —(CH$_2$CH$_2$O)$_\alpha$—(CH$_2$)$_\beta$CN; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; —(CH$_2$)$_\alpha$(CF$_2$)$_\gamma$CF$_3$; and an aryl group;

wherein $R_d$, $R_e$, $R_f$, $R_l$, $R_m$, $R_n$, $R_o$, $R_p$, $R_q$, $R_r$, $R_s$, $R_t$, $R_u$, $R_v$, $R_w$, and $R_x$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; —(CH$_2$CH$_2$O)$_\alpha$—(CH$_2$)$_\beta$OR$_{A1}$; —(CH$_2$CH$_2$O)$_\alpha$—(CH$_2$)$_\beta$NR$_{A2}$R$_{A3}$; —(CH$_2$CH$_2$O)$_\alpha$—(CH$_2$)$_\beta$CN; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; —(CH$_2$)$_\alpha$(CF$_2$)$_\gamma$CF$_3$; and an aryl group; wherein the hydrocarbon group is saturated or unsaturated;

wherein $R_g$, $R_h$, $R_i$, and $R_k$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; —(CH$_2$CH$_2$O)$_\alpha$—(CH$_2$)$_\beta$OR$_{A1}$; —(CH$_2$CH$_2$O)$_\alpha$—(CH$_2$)$_\beta$NR$_{A2}$R$_{A3}$; —(CH$_2$CH$_2$O)$_\alpha$—(CH$_2$)$_\beta$CN; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; an aryl group; —(CH$_2$)$_\alpha$(CF$_2$)$_\gamma$CF$_3$; —CO$_2$R$_d$; and —COR$_d$; wherein the hydrocarbon group is saturated or unsaturated;

wherein each aryl group is optionally independently selected from the group consisting of wherein $R_{A1}$, $R_{A2}$, $R_{A3}$, $R_{A4}$, $R_{A5}$, $R_{A6}$, $R_{A7}$, and $R_{A8}$ are the same or different and are each independently selected from the group consisting of H, a linear alkyl group, a branched alkyl group, and a cyclic alkyl group;

wherein E is selected from the group consisting of S, O, and $NR_s$;

wherein the alkyl group is optionally substituted or unsubstituted and optionally includes up to 25 carbon atoms;

wherein α is an integer that is greater than or equal to 0 and less than or equal to 25;

wherein β is an integer that is greater than or equal to 0 and less than or equal to 25; and wherein γ is an integer that is greater than or equal to 0 and less than or equal to 25.

6. A method as claimed in claim 5, wherein an amount of the compound is added to and mixed with the liquid-crystal mixture to yield a resulting mixture, wherein the amount of the compound is less than or equal to about 50% by weight of the resulting mixture.

7. A method for tuning birefringence of a liquid-crystal mixture, the method comprising adding to the liquid-crystal mixture a compound having a formula A:

(formula A)

wherein X is selected from the group consisting of wherein D is selected from the group consisting of $NR_aR_b$, $OR_a$, $SR_a$, $PR_aR_b$, and $R_c$;

wherein A is selected from the group consisting of:

wherein $R_a$, $R_b$, and $R_c$ are the same or different and are each independently selected from the group consisting of: H; a linear alkyl group; a branched alkyl group; a cyclic alkyl group; $-(CH_2CH_2O)_\alpha-(CH_2)_\beta OR_{A1}$; $-(CH_2CH_2O)_\alpha-(CH_2)_\beta NR_{A2}R_{A3}$; $-(CH_2CH_2O)_\alpha-(CH_2)_\beta CN$; $-(CH_2CH_2O)_\alpha-(CH_2)_\beta Cl$; $-(CH_2CH_2O)_\alpha-(CH_2)_\beta Br$; $-(CH_2CH_2O)_\alpha-(CH_2)_\beta I$; $-(CH_2CH_2O)_\alpha-(CH_2)_\beta$-Phenyl; $-(CH_2)_\alpha(CF_2)_\gamma CF_3$; and an aryl group;

wherein $R_d$, $R_e$, $R_f$, $R_l$, $R_m$, $R_n$, $R_o$, $R_p$, $R_q$, $R_r$, $R_s$, $R_t$, $R_u$, $R_v$, $R_w$, and $R_x$ are the same or different. and are each independently selected from the group consisting of: H; a linear hydrocarbon group; a branched hydrocarbon group; a cyclic hydrocarbon group; a linear alkyl group; a branched alkyl group; a cyclic alkyl group; $-(CH_2CH_2O)_\alpha-(CH_2)_\beta OR_{A1}$; $-(CH_2CH_2O)_\alpha-(CH_2)_\beta NR_{A2}R_{A3}$; $-(CH_2CH_2O)_\alpha-(CH_2)_\beta CN$; $-(CH_2CH_2O)_\alpha-(CH_2)_\beta Cl$; $-(CH_2CH_2O)_\alpha-(CH_2)_\beta Br$; $-(CH_2CH_2O)_\alpha-(CH_2)_\beta I$; $-(CH_2CH_2O)_\alpha-(CH_2)_\beta$-Phenyl; $-(CH_2)_\alpha(CF_2)_\gamma CF_3$; and an aryl group; wherein the hydrocarbon group is saturated or unsaturated;

wherein $R_g$, $R_h$, $R_i$, and $R_k$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; $-(CH_2CH_2O)_\alpha-(CH_2)_\beta OR_{A1}$; $-(CH_2CH_2O)_\alpha-(CH_2)_\beta NR_{A2}R_{A3}$; $-(CH_2CH_2O)_\alpha-(CH_2)_\beta CN$; $-(CH_2CH_2O)_\alpha-(CH_2)_\beta Cl$; $-(CH_2CH_2O)_\alpha-(CH_2)_\beta Br$; $-(CH_2CH_2O)_\alpha-(CH_2)_\beta I$; $-(CH_2CH_2O)_\alpha-(CH_2)_\beta$-Phenyl; an aryl group; $-(CH_2)_\alpha(CF_2)_\gamma CF_3$; $-CO_2R_d$; and $-COR_d$; wherein the hydrocarbon group is saturated or unsaturated;

wherein each aryl group is optionally independently selected from the group consisting of wherein $R_{A1}$, $R_{A2}$, $R_{A3}$, $R_{A4}$, $R_{A5}$, $R_{A6}$, $R_{A7}$, and $R_{A8}$ are the same or different and are each independently selected from the group consisting of H, a linear alkyl group, a branched alkyl group, and a cyclic alkyl group;

wherein E is selected from the group consisting of S, O, and $NR_s$;

wherein the alkyl group is optionally substituted or unsubstituted and optionally includes up to 25 carbon atoms;

wherein α is an integer that is greater than or equal to 0 and less than or equal to 25;

wherein β is an integer that is greater than or equal to 0 and less than or equal to 25; and wherein γ is an integer that is greater than or equal to 0 and less than or equal to 25.

8. A method as claimed in claim 7, wherein an amount of the compound is added to and mixed with the liquid-crystal mixture to yield a resulting mixture, wherein the amount of the compound is less than or equal to about 50% by weight of the resulting mixture.

9. A method for increasing a ∂n/∂T of a liquid-crystal mixture, the method comprising adding a compound to the liquid-crystal mixture to yield a resulting mixture; wherein the resulting mixture at about 20–30° C. has a ∂n/∂T larger than about 0.005, wherein n is a refractive index of the resulting mixture and T is a temperature of the resulting mixture in °C.; and wherein the compound has a formula A:

(formula A)

wherein X is selected from the group consisting of wherein D is selected from the group consisting of $NR_aR_b$, $OR_a$, $SR_a$, $PR_aR_b$, and $R_c$;

wherein A is selected from the group consisting of:

wherein $R_a$, $R_b$, and $R_c$ are the same or different and are each independently selected from the group consisting of: H; a linear alkyl group; a branched alkyl group; a cyclic alkyl group; —(CH$_2$CH$_2$O)$_\alpha$—(CH$_2$)$_\beta$OR$_{A1}$; —(CH$_2$CH$_2$O)$_\alpha$—(CH$_2$)$_\beta$NR$_{A2}$R$_{A3}$; —(CH$_2$CH$_2$O)$_\alpha$—(CH$_2$)$_\beta$CN; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; —(CH$_2$)$_\alpha$(CF$_2$)$_\gamma$ CF$_3$; and an aryl group;

wherein $R_d$, $R_e$, $R_f$, $R_l$, $R_m$, $R_n$, $R_o$, $R_p$, $R_q$, $R_r$, $R_s$, $R_t$, $R_u$, $R_v$, $R_w$, and $R_x$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; —(CH$_2$CH$_2$O)$_\alpha$—(CH$_2$)$_\beta$OR$_{A1}$; —(CH$_2$CH$_2$O)$_\alpha$—(CH$_2$)$_\beta$NR$_{A2}$R$_{A3}$; —(CH$_2$CH$_2$O)$_\alpha$—(CH$_2$)$_\beta$CN; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$ —(CH$_2$)$_\beta$-Phenyl; —(CH$_2$)$_\alpha$(CF$_2$)$_\gamma$CF$_3$; and an aryl group; wherein the hydrocarbon group is saturated or unsaturated;

wherein $R_g$, $R_h$, $R_i$, and $R_k$ are the same or different and are each independently selected from the group consisting of: H; a linear hydrocarbon group; a branched hydrocarbon group; a cyclic hydrocarbon group; a linear alkyl group; a branched alkyl group; a cyclic alkyl group; —(CH$_2$CH$_2$O)$_\alpha$—(CH$_2$)$_\beta$OR$_{A1}$; —(CH$_2$CH$_2$O)$_\alpha$—(CH$_2$)$_\beta$NR$_{A2}$R$_{A3}$; —(CH$_2$CH$_2$O)$_\alpha$—(CH$_2$)$_\beta$CN; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; an aryl group; —(CH$_2$)$_\alpha$(CF$_2$)$_\gamma$CF$_3$; —CO$_2$R$_d$; and —COR$_d$; wherein the hydrocarbon group is saturated or unsaturated;

wherein each aryl group is optionally independently selected from wherein $R_{A1}$, $R_{A2}$, $R_{A3}$, $R_{A4}$, $R_{A5}$, $R_{A6}$, $R_{A7}$, and $R_{A8}$ are the same or different and are each independently selected from the group consisting of H, a linear alkyl group, a branched alkyl group, and a cyclic alkyl group;

wherein E is selected from the group consisting of S, O, and NR$_s$;

wherein the alkyl group is optionally substituted or unsubstituted and optionally includes up to 25 carbon atoms;

wherein $\alpha$ is an integer that is greater than or equal to 0 and less than or equal to 25;

wherein $\beta$ is an integer that is greater than or equal to 0 and less than or equal to 25; and wherein $\gamma$ is an integer that is greater than or equal to 0 and less than or equal to 25.

10. A method as claimed in claim 9, wherein an amount of the compound is added to and mixed with the liquid-crystal mixture to yield the resulting mixture, wherein the amount of the compound is less than or equal to about 50% by weight of the resulting mixture.

11. A composition as claimed in claim 1, wherein the composition is a liquid-crystal composition.

12. A composition as claimed in claim 1, wherein $R_l$, $R_m$, $R_n$, $R_o$, $R_p$, $R_q$, $R_r$, $R_t$, $R_u$, $R_v$, $R_w$, and $R_x$ are each H; wherein A is C(CN)(CN); and wherein D is $R_y$ or OR$_y$, and wherein $R_y$ is selected from the group consisting of the linear alkyl group, the branched alkyl group, the cyclic alkyl group, and the aryl group.

13. A composition as claimed in claim 1, wherein the compound is selected from the group consisting of

(I)

(II)

(III)

14. A composition as claimed in claim 1, wherein A is selected from the group consisting of:

wherein $R_l$, $R_m$, $R_n$, $R_o$, $R_p$, $R_q$, $R_r$, $R_t$, $R_u$, $R_v$, $R_w$, $R_x$, and D are each independently selected from the group consisting of: H, methyl, ethyl, propyl, and butyl; and wherein $R_d$ is selected from the group consisting of methyl, ethyl, propyl, and butyl.

15. A composition as claimed in claim 12, wherein the composition is a liquid-crystal composition.

16. A composition as claimed in claim 13, wherein the composition is a liquid-crystal composition.

17. A composition as claimed in claim 14, wherein the composition is a liquid-crystal composition.

18. A method as claimed in claim 3, wherein $R_l$, $R_m$, $R_n$, $R_o$, $R_p$, $R_q$, $R_r$, $R_t$, $R_u$, $R_v$, $R_w$, and $R_x$ are each H; wherein A is C(CN)(CN); and wherein D is $R_y$ or $OR_y$, and wherein $R_y$ is selected from the group consisting of the linear alkyl group, the branched alkyl group, the cyclic alkyl group, and the aryl group.

19. A method as claimed in claim 3, wherein the compound is selected from the group consisting of

20. A method as claimed in claim 3, wherein A is selected from the group consisting of:

wherein $R_l$, $R_m$, $R_n$, $R_o$, $R_p$, $R_q$, $R_r$, $R_t$, $R_u$, $R_v$, $R_w$, $R_x$, and D are each independently selected from the group consisting of: H, methyl, ethyl, propyl, and butyl; and wherein $R_d$ is selected from the group consisting of methyl, ethyl, propyl, and butyl.

21. A method as claimed in claim 5, wherein $R_l$, $R_m$, $R_n$, $R_o$, $R_p$, $R_q$, $R_r$, $R_t$, $R_u$, $R_v$, $R_w$, and $R_x$ are each H; wherein A is C(CN)(CN); and wherein D is $R_y$ or $OR_y$, and wherein $R_y$ is selected from the group consisting of the linear alkyl group, the branched alkyl group, the cyclic alkyl group, and the aryl group.

22. A method as claimed in claim 5, wherein the compound is selected from the group consisting of

23. A method as claimed in claim 5,
wherein A is selected from the group consisting of:

wherein $R_l$, $R_m$, $R_n$, $R_o$, $R_p$, $R_q$, $R_r$, $R_t$, $R_u$, $R_v$, $R_w$, $R_x$, and D are each independently selected from the group consisting of: H, methyl, ethyl, propyl, and butyl; and
wherein $R_d$ is selected from the group consisting of methyl, ethyl, propyl and butyl.

24. A method as claimed in claim 7, wherein $R_l$, $R_m$, $R_n$, $R_o$, $R_p$, $R_q$, $R_r$, $R_t$, $R_u$, $R_v$, $R_w$, and $R_x$ are each H; wherein A is C(CN)(CN); and wherein D is $R_y$ or $OR_y$, and wherein $R_y$ is selected from the group consisting of the linear alkyl group, the branched alkyl group, the cyclic alkyl group, and the aryl group.

25. A method as claimed in claim 7, wherein the compound is selected from the group consisting of (I)

(II)

(III)

(IV)

26. A method as claimed in claim 7,
wherein A is selected from the group consisting of:

wherein $R_l$, $R_m$, $R_n$, $R_o$, $R_p$, $R_q$, $R_r$, $R_t$, $R_u$, $R_v$, $R_w$, $R_x$, and D are each independently selected from the group consisting of: H, methyl, ethyl, propyl, and butyl; and
wherein $R_d$ is selected from the group consisting of methyl, ethyl, propyl, and butyl.

27. A method as claimed in claim 9, wherein $R_l$, $R_m$, $R_n$, $R_o$, $R_p$, $R_q$, $R_r$, $R_t$, $R_u$, $R_v$, $R_w$, and $R_x$ are each H; wherein A is C(CN)(CN); and wherein D is $R_y$ or $OR_y$, and wherein $R_y$ is selected from the group consisting of the linear alkyl group, the branched alkyl group, the cyclic alkyl group, and the aryl group.

28. A method as claimed in claim 9, wherein the compound is selected from the group consisting of (I)

(II)

(III)

(IV)

29. A method as claimed in claim 9,
wherein A is selected from the group consisting of:

wherein $R_l$, $R_m$, $R_n$, $R_o$, $R_p$, $R_q$, $R_r$, $R_t$, $R_u$, $R_v$, $R_w$, $R_x$, and D are each independently selected from the group consisting of: H, methyl, ethyl, propyl, and butyl; and
wherein $R_d$ is selected from the group consisting of methyl, ethyl, propyl, and butyl.

30. The composition as claimed in claim 1, wherein the compound is colorless or virtually colorless.

31. The composition as claimed in claim 1, wherein the compound has an absorption loss in a visible spectrum at approximately 20–30° C. of greater than or equal to 0% and less than or equal to about 5%.

32. The composition as claimed in claim 1, wherein the compound has an absorption loss in a visible spectrum at approximately 20–30° C. of greater than or equal to 0% and less than or equal to about 1%.

33. The composition as claimed in claim 1, wherein the compound has an absorption loss in a visible spectrum at approximately 20–30° C. of greater than or equal to 0% and less than or equal to about 0.01%.

34. The composition as claimed in claim 1, wherein A is C(CN)(CN).

35. The method as claimed in claim 3, wherein A is C(CN)(CN).

36. The method as claimed in claim 5, wherein A is C(CN)(CN).

37. The method as claimed in claim 7, wherein A is C(CN)(CN).

38. The method as claimed in claim 9, wherein A is C(CN)(CN).

39. The composition as claimed in 14, wherein A is C(CN)(CN).

40. The method as claimed in claim 20, wherein A is C(CN)(CN).

41. The method as claimed in claim 23, wherein A is C(CN)(CN).

42. The method as claimed in claim 26, wherein A is C(CN)(CN).

43. The method as claimed in claim 29, wherein A is C(CN)(CN).

44. The method as claimed in claim 2, wherein A is C(CN)(CN).

45. The method as claimed in claim 4, wherein A is C(CN)(CN).

46. The composed as claimed in as 6, claim wherein A is C(CN)(CN).

47. The method as claimed in claim 8, wherein A is C(CN)(CN).

48. The method as claimed in claim 10, wherein A is C(CN)(CN).

49. The composition as claimed in claim 11, wherein A is C(CN)(CN).

50. The composition claimed in claim 15, wherein A is C(CN)(CN).

51. The composition as claimed in claim 16, wherein A is C(CN)(CN).

52. The composition as claimed in claim 17, wherein A is C(CN)(CN).

53. The composition as claimed in claim 30, wherein A is C(CN)(CN).

54. The composition as claimed in claim 31, wherein A is C(CN)(CN).

55. The composition as claimed in claim 32, wherein A is C(CN)(CN).

56. The composition as claimed in claim 33, wherein A is C(CN)(CN).

* * * * *